US00RE42288E

(19) United States
(12) Reissued Patent
Degioanni

(10) Patent Number: US RE42,288 E
(45) Date of Reissued Patent: Apr. 12, 2011

(54) EMERGENCY FACILITY VIDEO-CONFERENCING SYSTEM

(75) Inventor: Joseph J. Degioanni, Houston, TX (US)

(73) Assignee: Emtel, Inc., Houston, TX (US)

(21) Appl. No.: 12/290,124

(22) Filed: Oct. 24, 2008

Related U.S. Patent Documents

Reissue of:
(64) Patent No.: 7,129,970
Issued: Oct. 31, 2006
Appl. No.: 10/396,635
Filed: Mar. 25, 2003

U.S. Applications:
(63) Continuation of application No. 10/118,445, filed on Apr. 8, 2002, now abandoned, which is a continuation of application No. 09/527,774, filed on Mar. 17, 2000, now Pat. No. 6,369,847.

(51) Int. Cl.
*H04N 7/14* (2006.01)

(52) U.S. Cl. ..... 348/14.01; 348/14.05; 348/14.08; 348/14.09; 379/106.02; 600/300

(58) Field of Classification Search .... 348/14.01–14.16; 379/37–38, 106.01, 106.02; 600/300, 301, 600/509, 513; 128/903, 904; 709/204, 230, 709/240, 205; 700/17, 65, 68
See application file for complete search history.

(56) References Cited

U.S. PATENT DOCUMENTS 4,113,331 A 9/1978 Derdszinski et al.
4,237,344 A 12/1980 Moore
4,719,513 A 1/1988 Peterson
(Continued)

FOREIGN PATENT DOCUMENTS

EP 505627 A2 9/1992
(Continued)

OTHER PUBLICATIONS

Viegas, S.F., et al., "*Telemedicine, Practicing in the Information Age*," Lipincott-Raven Publishers, Philadelphia (1998).

(Continued)

*Primary Examiner* — Melur Ramakrishnaiah
(74) *Attorney, Agent, or Firm* — Gary L. Bush; Brett T. Cooke; Andrews Kurth LLP

(57) ABSTRACT

A medical video-teleconferencing and treatment system, having a central video-conferencing station and one or more remote video-conferencing stations and a communications link establishing video-conferencing communication therebetween. A central video monitor and audio system is located at the central video-conferencing station, and a controller unit is coupled with the communications link. The remote video-conferencing stations each have a mobile emergency center cart including a remote video monitor and audio system and a video-conferencing camera controlled by the controller unit via the communications link and capable of responding to control signals of the controller unit for panning and zoom movement of said video-conferencing camera by a medical practitioner located at the central video-conferencing station. The arrangement enables the medical practitioner to observe and to diagnose the condition of the patient and direct the medical personnel of the selected video-conferencing station to provide treatment of the patient.

20 Claims, 9 Drawing Sheets

U.S. PATENT DOCUMENTS

| | | | | |
|---|---|---|---|---|
| 4,755,881 | A | 7/1988 | Bartlett | |
| 5,390,238 | A | 2/1995 | Kirk et al. | |
| 5,434,611 | A | 7/1995 | Tamura | |
| 5,441,047 | A | 8/1995 | David et al. | |
| 5,481,297 | A | 1/1996 | Cash et al. | |
| 5,489,938 | A | 2/1996 | Maruyama et al. | |
| 5,544,649 | A | 8/1996 | David et al. | |
| 5,553,609 | A * | 9/1996 | Chen et al. | 600/301 |
| 5,585,839 | A | 12/1996 | Ishida et al. | |
| 5,594,786 | A | 1/1997 | Chaco et al. | |
| 5,687,717 | A | 11/1997 | Halpern et al. | |
| 5,767,897 | A | 6/1998 | Howell | |
| 5,785,650 | A | 7/1998 | Akasaka et al. | |
| 5,801,755 | A | 9/1998 | Echerer | |
| 5,802,494 | A | 9/1998 | Kuno | |
| 5,810,747 | A | 9/1998 | Brudny et al. | |
| 5,810,755 | A | 9/1998 | LeVeen et al. | |
| 5,822,544 | A | 10/1998 | Chaco et al. | |
| 5,872,922 | A | 2/1999 | Hogan et al. | |
| H1790 | H | 3/1999 | Coleman | |
| 5,877,675 | A | 3/1999 | Rebstock et al. | |
| 5,900,907 | A | 5/1999 | Malloy et al. | |
| 5,961,446 | A | 10/1999 | Beller et al. | |
| 5,963,245 | A | 10/1999 | McDonald | |
| 5,987,519 | A * | 11/1999 | Peifer et al. | 709/230 |
| 5,990,932 | A | 11/1999 | Bee et al. | |
| 6,014,432 | A | 1/2000 | Modney | |
| 6,024,699 | A | 2/2000 | Surwit et al. | |
| 6,046,761 | A | 4/2000 | Echerer | |
| 6,101,478 | A | 8/2000 | Brown | |
| 6,151,521 | A | 11/2000 | Guo et al. | |
| 6,168,563 | B1 | 1/2001 | Brown | |
| 6,319,200 | B1 | 11/2001 | Lai et al. | |
| 6,369,847 | B1 | 4/2002 | James et al. | |
| 6,398,727 | B1 | 6/2002 | Bui et al. | |
| 6,437,826 | B1 | 8/2002 | Arnold | |
| 6,454,705 | B1 | 9/2002 | Cosentino et al. | |
| 6,490,490 | B1 | 12/2002 | Uchikubo et al. | |
| 6,589,169 | B1 | 7/2003 | Surwit et al. | |
| 6,638,218 | B2 * | 10/2003 | Bulat | 600/300 |
| 6,648,820 | B1 | 11/2003 | Sarel | |
| 6,731,324 | B2 | 5/2004 | Levy | |
| 6,765,991 | B1 | 7/2004 | Hanuschak et al. | |
| 6,804,656 | B1 | 10/2004 | Rosenfeld et al. | |
| 6,820,057 | B1 | 11/2004 | Loch et al. | |
| 6,870,484 | B1 | 3/2005 | Brinsfield et al. | |
| 7,129,970 | B2 | 10/2006 | James et al. | |
| 2001/0037366 | A1 | 11/2001 | Webb et al. | |
| 2002/0188179 | A1 | 12/2002 | Bulat | |
| 2003/0179287 | A1 | 9/2003 | Kozic et al. | |
| 2003/0179292 | A1 | 9/2003 | Provost et al. | |
| 2004/0070615 | A1 | 4/2004 | Ewing et al. | |

FOREIGN PATENT DOCUMENTS

| | | | |
|---|---|---|---|
| EP | 917364 | A2 | 5/1999 |
| JP | 07-274148 | A | 10/1995 |
| JP | 407274148 | A * | 10/1995 |
| JP | 08-215158 | | 8/1996 |
| JP | 10-137197 | A | 5/1998 |
| WO | WO 96/24284 | A1 | 8/1996 |
| WO | WO 96/28086 | A1 | 9/1996 |
| WO | WO 97/12474 | A1 | 4/1997 |
| WO | WO 97/12544 | A1 | 4/1997 |
| WO | WO 98/08203 | A1 | 2/1998 |
| WO | WO 99/14882 | A2 | 3/1999 |
| WO | WO 99/59469 | A1 | 11/1999 |
| WO | WO 01/30231 | A2 | 5/2001 |

OTHER PUBLICATIONS

Crump, W.J., et al., *Communication in Integrated Practice Networks: Using Interactive Video Technology to Build the Medical Office Without Walls,* Texas Med. vol. 93, No. 3, pp. 70-75, Galveston, TX (Mar. 1997).

Fasken Martineau DuMoulin LLP, "Submission Pursuant to Section 34.1 of the Canadian Patent Act" (Ser. No. 2,401,902, Appl. Emtel, Inc., Title: Emergency Facility Video-Conferencing System, Filed Oct. 6, 2000); Canada (Feb. 7, 2008).

Gammon, D., et al., *Videoconferencing in Psychiatry: A Survey of Use in Northern Norway,* J. of Telemed. and Telecare vol. 2, No. 4 (1996).

Myhill, K., *Telepsychiatry in Rural South Australia,* J. of Telemed. and Telecare vol. 2, No. 4 (1996).

Doze, S., et al., *Evaluation of a Telepsychiatry Pilot Project,* J. of Telemed. and Telecare vol. 5, No. 1 (1999).

Elford, D., *Telemedicine in Northern Norway,* J. of Telemed. and Telecare vol. 3, No. 1 (1997).

Tachakra, S., et al., *A Protocol for Telemedical Consultation,* J. of Telemed. and Telecare vol. 3, No. 3 (1997).

Canada International, *The Latest in Videoconferencing Equipment,* Canada, (Apr. 1999).

"Defendants Specialists on Call, Inc., Tele-Med Dox, LLC, and Doctors Telehealth Network, Inc.'s Preliminary Invalidity Contentions Under P.R. 3-3 and Document Production Under P.R. 3-4," C.A. No. 4:07-cv-01798; *Emtel, Inc.,* v. *Lipidlabs, Inc., et al.;* in the U.S. Dist. Ct. for the So. Dist. of TX, Houston Div., Houston, TX (Jun. 20, 2008).

Elford, R., *Telemedicine Activities at Memorial University of Newfoundland: A Historical Review,* 1975-1997, Telemed. J. vol. 4, No. 3 (1998).

Blignault, I., *Multipoint Videoconference in Health—A Review of Three Years' Experience in Queensland Australia,* Telemed. J. vol. 6, No. 2 (2000).

Pavlopoulos, S., et al., *A Novel Emergency Telemedicine System Based on Wireless Communication Technology Ambulance*, IEEE Transactions On Information Technology In Biomedicine, vol. 2, No. 4 (1998).

Shafqat, S., *Role for Telemedicine in Acute Stroke,* 30 Stroke 2141 (1999).

Levine, S., et al., "*Telestroke"—The Application of Telemedicine for Stroke,* 30 Stroke 464 (1999).

Hassol, A., et al., *Rural Telemedicine Data-Image Transfer Methods and Purposes of Interactive Video Sessions,* 4 J. of the Am. Med. Informatics Assoc. 36-37 (1997).

Wilkinson, A., et al., *Beyond Telemedicine,* Corrections Today (Apr. 1998).

Balch, D., et al., *Telemedicine Expanding the Scope of Health Care Information,* J. of the Am. Med. Informatics Assoc., vol. 4, No. 1 (Jan.-Feb. 1997).

Scannell, K., *Telemedicine—Past, Present, Future—Jan. 1966 Through Mar. 1995,* Current Bibliographies In Medicine, Nat'l Lib. of Med. (1995).

McNeill, K., et al., *Arizona Telemedicine Program,* J. of the Am. Med. Informatics Assoc., vol. 5, No. 5 (Sep.-Oct. 1998).

Yellowlees, P., *Telemedicine Applications in an Integrated Mental Health Service Based at a Teaching Hospital,* 2 J. of Telemed. & Telecare Journal of Telemedicine and Telecare 205-09 (1996).

Lockheed Missiles & Space Co., STARPAHC Systems Report (NASA-CR-151578) (Oct. 1977).

Rosenthal, L.H., U.S. District Judge: "Memorandum and Order," C.A. No. H-07-1798; *Emtel, Inc.* v. *Lipidlabs, Inc., et al.;* In the U.S. Dist. Ct. for the So. Dist. of TX, Houston Div., Houston, TX (Sep. 30, 2008).

Choi, John Y., et al., *Telemedicine Physician Providers: Augmented Acute Stroke Care Delivery in Rural Texas: An Initial Experience,* Telemedficine Journal and e-Health, 2004. 10(supplement 2): S-90-S-94. http://www.liebertonline.com/do/abs/10.1089/tmj.2004.10.S-90.

Raine, M., *Telemedicine Enables UT Doctors to Remotely Treat Stroke Patients,* Distinctions (Jan. 2004) http://publicaffairs.uth.tmc.edu/distinctions/archive/2004/January/telemedicine.html.

Sayewitz, R., *JFK Medical Invests in Telemedicine Technology,* So. Fl. Business J. (Jun. 10, 2002) http://southflorida.bizjournals.com/southflorida/stories/2002/06/10/focus1.html.

Zocco, G., et al., *TIMTEM Project: Our experience in a remote area,* Telemedicine J. and e-Health, 9(1), pp. 117-121 (2003) (Abstract).

Texas Tech U., *Telemedicine,* (2006) http://www.ttuhsc.edu/telemedicine/default.htm.

UTMB Telehealth Center, TeleHealth News Articles,, *Texas Prison Medical System Offers Answers for Healthcare Crisis;* Medical News Today, (Aug. 1, 2004).

U.S. Dept. of Justice, *Telemedicine Can Reduce Correctional Health Care Costs, An Evaluation of a Prison Telemedicine Network,* Research Report, Abt Associates, Inc., Washington (Mar. 1999).
Corr. from American Telemedicine Association to The Hon. Jon W. Dudas, Under Sec. of Comm. for IP and Dir. of USPTO, Feb. 29, 2008.
MediaMax™, User's Guide and System Administrator's Reference, VTEL Communication Without Boundaries, VTEL Corp., (Feb. 1996).
VTEL, MCU-II, Quick Reference Card.
MCU-II™ —Operations Manual, by VTEL, Austin, TX (Mar. 1994).
Rogers, F. B., et al., *The use of telemedicine for real-time video consultation between trauma center and community hospital in a rural setting improves early trauma care: preliminary results,* J. Trauma, Vermont (Dec. 2001) (Abst).
Hajek, M., et al, *Multi-site interventional real-time procedure demonstrations with the use of integrated services digital network connections,* Cardiovasc Intervent Radiol, Czech Rep. (Sep-Oct. 2001).
Yoo, S.K., et al., *Evaluation of two mobile telemedicine systems in the emergency room,* J. Telemed. Telecare, Korea (2003).
Norris, T.E., et al., *Low-bandwidth, low-cost telemedicine consultations in rural family practice,* J. Am. Board Fam. Pract., Washington (Mar.-Apr. 2002).
Nagatuma, H., *Development of an Emergency Medical Video Multiplexing Transport System* (*EMTS*): *aiming at the nation-wide prehospital care in ambulance,* J. Med. Syst., Japan (Jun. 2003).
Tachakra, S., et al., *A pilot study of the technical quality of telemedical consultations for remote trauma management,* J. Audiov Media Med., London (Mar. 2001).
Tachakra, S., et al., *Remote trauma management—setting up a system,* J. Telmed. Telecare, London (1996).
Rosenfeld, B.A., et al., *Intensive care unit telemedicine: alternate paradigm for providing continuous intensivist care,* Crit. Care Med., Maryland (Dec. 2000).
Benger, J., *A review of minor injuries telemedicine,* J. Telemed. Telecare, United Kingdom (1999).
Stamford, P., et al., *The significance of telemedicine in a rural emergency department,* IEEE Eng. Med. Biol. Mag., N. Carolina (Jul.-Aug. 1999).
Polycom, *Telemedicine—Bridging distance of world communities without compromising care quality and access to specialists* http://www.polycom.com/solutions/0,,pw-4855,00.html.
Greenberg, A. *The Evolving Role of Videoconferencing in Healthcare; Pushing the boundaries of Knowledge Transfer,* Wainhouse Research (Apr. 2004).
ATA News and Resources, *Overview of Telemedicine,* (Nov. 8, 2006) http://www.atmeda.org/news/overview.htm.
ATA Telemedicine Association, *ATA Telemedicine Buyer's Guide; Telemedicine Product & Svc. Providers,* (2007) http://www.atmeda.org/news/buyersguide.htm.
ATA News and Resources, *ATA Media Info. Telemedicine Reduces the Cost of Healthcare,* (2005) http://www.americantelemed.org/news/mediaguide/costefficiency.htm.
Perednia, D.A., *Telemedicine Technology and Clinical Applications,* J. of the Am. Med. Assoc. (Feb. 8, 1995).
Merrell, R.C., *Telemedicine in the 90's: Beyond the Future,* J. of Medical Systems, vol. 19, No. 1 (Feb. 1995).
Kurtz, G.L., *The Future of Telecommunications in Rural Health Care,* J. of Healthcare Info & Mgmt. Sys., vol. 8, No. 3 (Summer 1994).
Bakalar, R.S., *Operational Telemedicine, Naval Telemedicine Business Office,* (Power Point Presentation), Dept. of Navy, Maryland (Aug. 2001).
Wolfshohl, K., *Better Care for Families* (*For those in remote areas, good health care isn't the problem it once was.*), Progressive Farmer, (Jul. 2000).
Watts, J., *Wide Open Spaces; Remote Access,* Pulse (Tex. Tech Health Sci. Ctr) (Summer 2000).
Stoneham, L., *The Long Hand of Healing* (*Telemedicine reaches into the distant small towns of Texas to provide the best in medical care.*), (Aug. 2000).
Brown, N., *Telemedicine 101—Telemedicine Coming of Age,* Telemedicine Information Exchange (TIE), (Sept. 28, 1996, up. Jan. 13, 2005) http://tie.telemed.org/articles/article.asp?path=telemed101&article=tmcoming_nb-tie96.xml.
Brown, N., *A Brief History of Telemedicine,* Telemedicine Information Exchange (TIE), (May 30, 1995) http://tie.telemed.org/articles/article.asp?path=articles&article=tmhistory_nb-tie95.xml.
Grigsby, B., PhD., *In Pursuit of a Market Analysis for Telemedicine,* Telemedicine Information Exchange (TIE), (Jun. 6, 2000) http://tie.telemed.org/articles/article.asp?path=articles&article=telemedMarketAnalysis_bg_tie00.xml.
Wachter, G.W., *Telemedicine 101—Needs Assessment: A Key to Building Better Telemedicine Programs,* Telemedicine Information Exchange (TIE), (Oct. 25, 2000) http://tie.telemed.org/articles/article.asp?path=telemed101&article=needsAssess_gw_tie00.xml.
Suleiman, A.B., PhD., Telemedicine & Telehealth Networks National Networks (Power Point Presentation), Michigan (Aug. 23-25, 2001 Conf.).
Texas Tech U., *Telemedicine Comes to El Paso,* Telemedicine Report, vol. 3, No. 2 (Jul. 2001).
Texas Tech U., *Providing Burn Care in El Paso,* Telemedicine Report, vol. 4, No. 1 (Jan. 2002).
Medical Industry Week, *Telemedicine Technology Reaches New Heights,* Med. Indus. Wk., MDIS Publs. Ltd. (Aug. 24, 1999).
Globe and Mail, *Children's Miracle Network, Telehealth Serves Remote Areas,* Globemail C4, Section: Advertising Special Report, Canada, (Jun. 4, 1999).
Campbell, S., *Will Telemedicine Become as Common as the Stethoscope?,* Health Care Strategic Mgmt., The Business Word, Inc., vol. 13, Is. 4 (Apr. 1, 1997).
Quayle, C., *Make the Connection, Telemedicine could be made more effective by using a wise technology manager,* Health Fac. Mgmt., Am. Hospital Pub., Inc. (Apr. 1997).
Borsellino, M., *Provinces share telemedicine plans for future* (*Nova Scotial, New Brunswick, Manitoba and NW Territories*), Med. Post, Micromedia Ltd. (Mar. 11, 1997).
Dakins, D.R., *ATA approves set of clinical guidelines for home-based care,* Telehealth Mag. 15, Miller Freeman, Inc. (Dec. 1, 1998).
Telehealth, *Rapid Transmission. Mental healthcare tops fist of consulting services in ATSP report,* Telehealth Mag. 9, Miller Freeman, Inc., vol. 5; Is. 1 (Feb. 1999).
Dakins, D.R., *HFCA releases new blueprint for teleconsult pay scheme,* Telehealth Mag. 9, vol. 5; Is. 1, Miller Freeman, Inc. (Feb. 1, 1999).
Hoffman, E., *Latrobe Area Hospital Unveils Link to Children's,* Pitt. Post-Gazette B2, PG Pub. Co. (Nov. 19, 1999).
Dakins, D., et al., *The Envelope, Please: Top 10 Telemedicine Programs for 1998,* Telehealth Mag. 32, vol. 4; Is. 7, Miller Freeman, Inc. (Dec. 1, 1998).
Biotech, *Avistar Video Technology Used to Perform Surgery,* Biotech Equip. Update, vol. 6; Is. 7, Worldwide Videotex (Jul. 1, 1998).
Quayle, C., *MedTV* (*Used for everything from video consultations to teleradiology . . .* ), Health Fac. Mgmt. 34, vol. 12; Is. 10, Am. Hosp. Publ. Inc. (Oct. 1999).
Cisco Systems, *Acuson demonstrating digital telemedicine,* Med. Indus. Wk., MDIS Public. Ltd. (Feb. 23, 1999).
Tweed, V., *The brave new reality of telemedicine,* Bus & Health 34, vol. 16; Is. 9, Med. Econ. Publ. Co. (Sep. 1, 1998).
Felix, S., *Telemedicine: the next best thing,* Can. Healthcare Mgr., Micromedia Ltd. (Jul. 1998).
Gasch, A., *The present offers a small glimpse of telemedicine's future,* BBI Newsl., Am. Health Cons. (May 1, 1998).
BBI Newsletter, *Welcome to the ROC* (*Remote Obstetrical Care*), BBI Newsl., vol. 20; Is. 3, Am. Health Cons. (Mar. 1, 1997).
Dakins, D.R., *Increased investment and incremental expansion fuels optimism,* Telehealth Mag. 28, Miller Freeman, Inc. (Jun. 1, 1999).
Kincade, K., *Top 10 Telemedicine programs for 1999: Experience pays off,* Telehealth Mag. 12, vol. 5; Is. 7, Miller Freeman, Inc. (Dec. 1, 1999).

Kincade, K., *Tinkering continues on Medicare payment rule,* Telehealth Mag. 7, vol. 5; Is. 3, Miller Freeman, Inc. (Jun. 1, 1999).
Craig, J., et al., *The Cost-Effectiveness of Teleneurology Consultations for Patients Admitted to Hospitals Without Neurologists on site. 1: A Retrospective Comparison of the Case-Mix and Management at Two Rural Hospitals,* J. of Telemed. and Telecare, vol. 6, Supp. 1, Omagh, Uk (2000).
Duke, J.H. Jr., et al., *Disaster Relief and Emergency Medical Services Project* (*Dreams TM*) : *Digital EMS,* (Final Report) U. of Tx. Health Sciences Ctr., Houston, TX (Oct. 2000).
McDonald, D., et al., *Can Telemedicine Reduce Spending and Improve Prisoner Health Care?,* U.S. Dept. of Justice, Nat'l Inst. of Justice J. (Apr. 1999).
"Is There a Doctor in the House?" *National Law Enforcement and Corrections Technology Center*, TECH b•e•a•t, (dedicated to reporting developments in technology for law enforcement, corrections, and forensics) Rockville, MD (Spring 1998).
"Correctional Health Care Services" UTMB Electronic Health Network, U. of Texas Medical Branch, Galveston, TX.
Phipps, J.L., *Distance Dollars: Physicians Try to Improve Telemedicine's Profitability,* Crain Comm., Inc. Modern Phys. , Doc. 78 p. 38 (Nov. 1, 2001).
The Associated Press, *Telemedicine Expands Among Ohio Prisons,* LRP Publs. Corrections Professional, Doc. 58, vol. 8, No. 2, Ohio (Sep. 6, 2002).
Brunicardi, B.O., *Financial Analysis of Savings from Telemedicine in Ohio's Prison System,* Comparative Study, Nat'l Library of Med. Medline Database, Doc. 16 of 21, Telemed J., 4(1): 49-54, Ohio (Spring 1998).
Mekhjian, H., et al., *An Ohio Telemedicine System for Prison Inmates: A Case Report,* Telemed J., vol. 2, No. 1, pp. 17-23, Ohio (1996).
Baker, T., *Telemedicine: Dodge County,* Center for Telehealth, Med. Coll. of GA, (Oct. 2005) http://www.mcg.edu/telehealth/DodgeCty.htm.
Evolution of Telemedicine in Georgia, Center for Telehealth, Med. Coll. Of GA (Oct. 2005) http://www.mcg.edu/telehealth/Evolution.htm.
Arizona Telemedicine Program: U. Of Arizona http://www.telemedicine.arizona.edu/urogram/description.html.
Thornton, D. Mc., *OIG Advisory Opinion No. 99-14* (re: a rural telemedicine network . . . ) (Dec. 28, 1999).
ATA 2007 Final Program, ATA's 12th Ann. Interna'l Mtg. and Trade show, Nashville, TN (May 13-15, 2007).
Images-on-Call and HIPAA—A Statement of Practice; HIPAA Recommendations for IOC Teleradiology Customers.
CIT MVIC II, *Mobile Video Interactive Companion II . . . Extends your video conference . . . wirelessly,* West Chester, OH.
Tandberg Features, *Tandberg Advantage: Security;* Tandberg Expressway and Firewalls.
LaMonte, M.P., et al., *Shortening Time to Stroke Treatment Using Ambulance Telemedicine: TeleBAT,* J. of Stroke and Cerebrovascular Diseases, vol. 13, No. 4 (Jul.Aug. 2004): pp. 148-154.
Wilkinson, R.A., et al., *Beyond Telemedicine, Ohio Expands Its Use of Videoconferencing Technologies,* Corrections Today, Am. Correctional Assoc., Ohio (Apr. 1998) http://www.drc.state.oh.us/web/Articles/article33.htm.
Rosa, J., *Telemedicine,* Legislative Budget Office, Policy Brief, vol. 1, No. 6, Ohio (Jan. 29, 1999).
"Ohio Prisoners Visit the Doctor Via Telemedicine," News Release, Ohio Dept. of Rehab. And Corr., Ohio (Aug. 2, 2001) http://www.drc.state.oh.us/Public/press98.htm.

* cited by examiner

FIG. 3
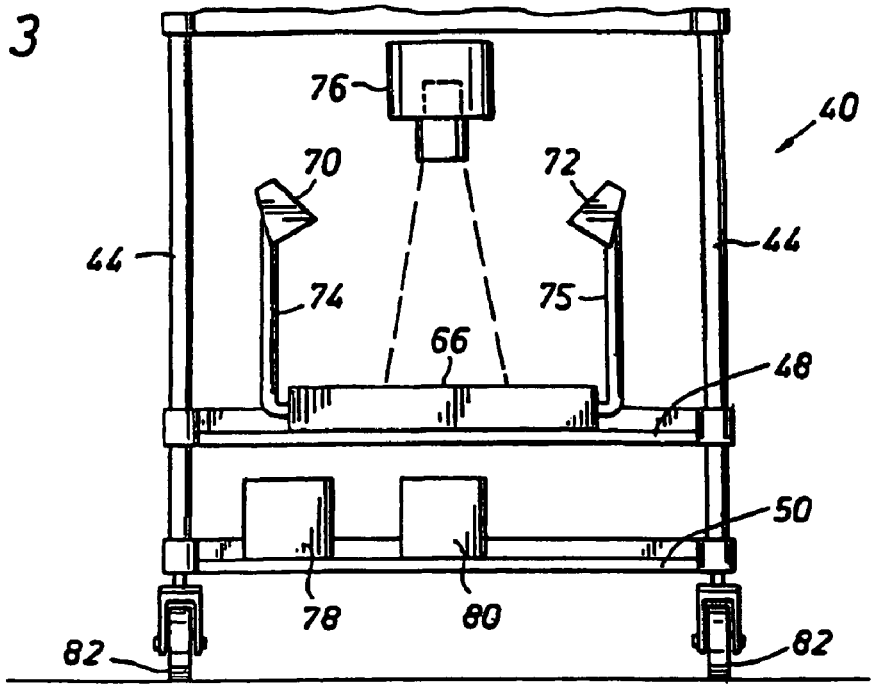
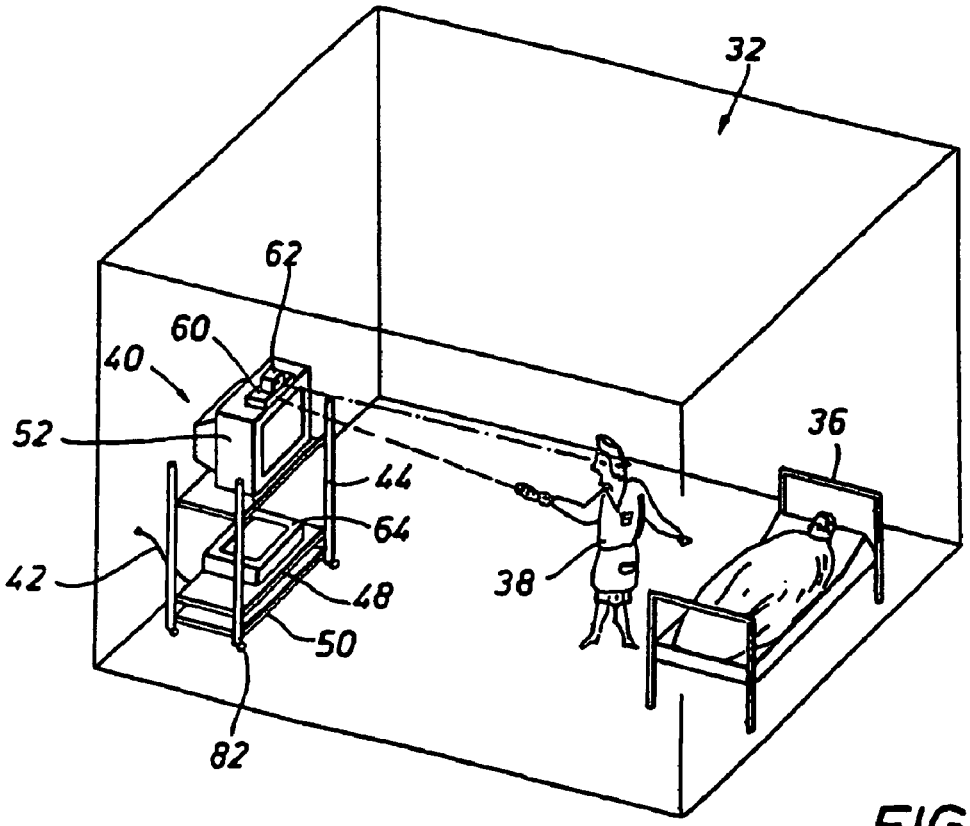
FIG. 4

FIG. 13
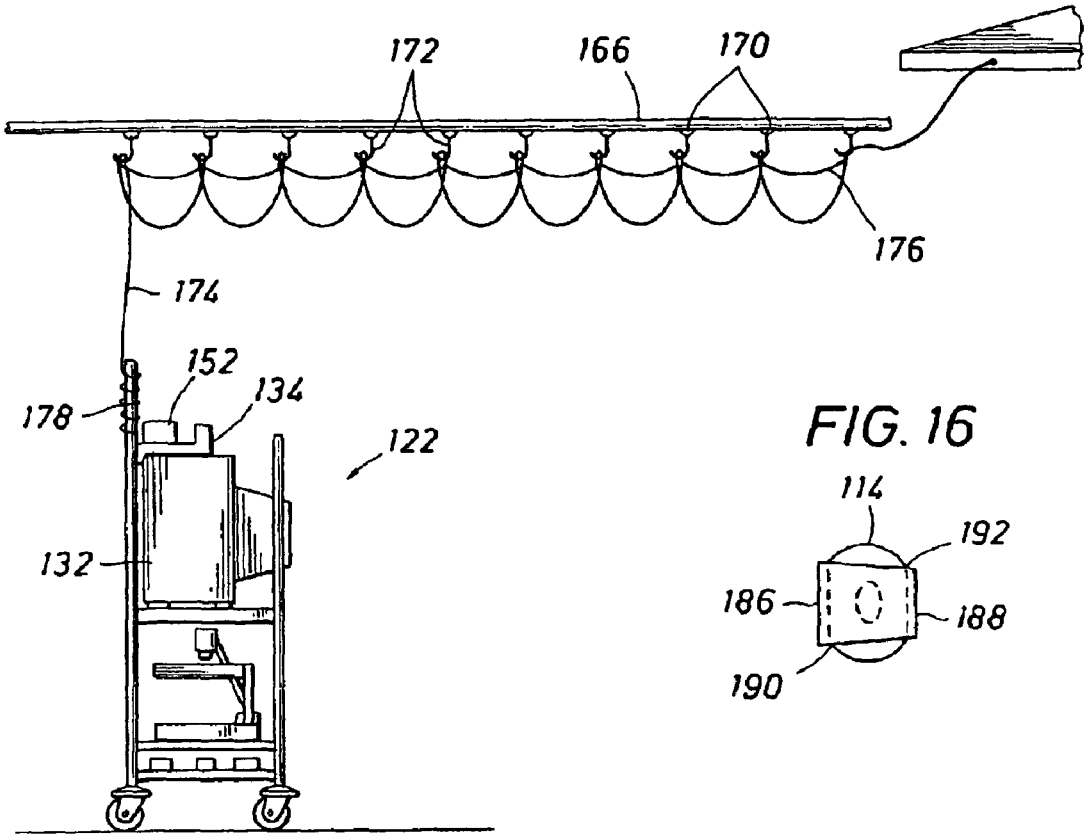
FIG. 16
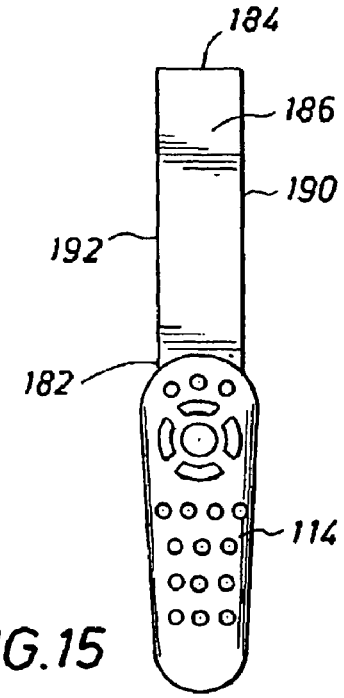
FIG. 15
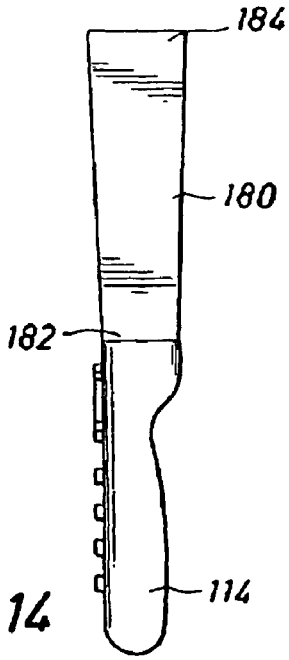
FIG. 14

EMERGENCY FACILITY VIDEO-CONFERENCING SYSTEM

Matter enclosed in heavy brackets [ ] appears in the original patent but forms no part of this reissue specification; matter printed in italics indicates the additions made by reissue.

This application is a continuation of application number U.S. Ser. No. 10/118,445 filed on Apr. 8, 2002, now abandoned, which is a continuation of application Ser. No. 09/527,774 filed on Mar. 17, 2000, now U.S. Pat. No. 6,369,847, the priority of which is claimed.

BACKGROUND OF THE INVENTION

1. Field of the Invention

This invention relates generally to the field of video-conferencing wherein a two-way video and audio system is provided enabling one or more parties at one location to be in communication with one or more parties at another location. More specifically, the present invention pertains to a medically related video-conferencing system that is particularly suited to emergency medical activities and enables a physician at a central location to diagnose and control treatment of patients located at one or more remote medical facilities. Even more specifically, the present invention concerns the use of portable video-conferencing units at each of one or more remote emergency facility locations and having components, such as a video-conferencing CODEC (Compressor/Decompressor), that can be controlled by the physician from the physician's central location to thus enable efficient diagnosis of the patient and to ensure proper treatment of the patient by the medical personnel of the remote facility.

2. Description of the Prior Art

Although the field of video-conferencing has been under development only in recent years, a number of processes, procedures and interactive communications systems have been developed to enable video-conferencing in a wide variety of commercial environments. Examples of methods and apparatus associated with video-conferencing are presented in U.S. Pat. No. 4,719,513 of Peterson, U.S. Pat. No. 5,489,938 of Maruyama, et al. U.S. Pat. No. 5,767,897 of Howell, and U.S. Pat. No. 5,900,907 of Malloy, et al. U.S. Pat. No. 4,719,513 discloses a compact video system in the form of a mobile cart having compartments for containing video and video recording equipment such as a video camera and video recorder as well as a battery for providing a source of electrical power for operation of the video and video recording system (VCR) in remote conditions and to facilitate ease of using the equipment. The mobile cart device is also provided with a camera mount enabling the video camera to be appropriately mounted on the mobile cart for use. U.S. Pat. No. 5,489,938 discloses television conference apparatus in the form of a mobile cart which has a number of storage compartments within which apparatus such as a video camera, a manuscript table, a fax machine, etc. may be stored and may be subsequently used simply by opening compartment doors, operating lights or positioning equipment.

U.S. Pat. No. 4,755,881 also discloses a mobile cart within which various video apparatus such as a video monitor, VCR, battery, video camera, etc. may be stored so as to be readily available for use. U.S. Pat. No. 5,900,907 discloses a video-conferencing unit intended to be mounted to or supported by a video monitor and being designed with a differential signal sensing sound system enabling the video camera, or its lens to be automatically directed to the source of the sound, i.e., such as an individual speaking at a video conference, by the differential sound signal.

An interactive video/audio communications system has also been developed for medical treatment of remotely located patients as set forth in U.S. Pat. No. 5,810,755. In this case, a medical practitioner's station is in communication with a medical treatment station via video-conferencing apparatus each having video cameras, audio speakers, etc. This particular medical apparatus is particularly designed for ensuring identification of the patient and for ensuring payment for medical services via credit card or insurance card.

When a remotely located patient is being treated, especially during emergency treatment at a remotely located emergency facility, the patient's condition may not be well known. It is thus desirable for a medical practitioner, located at a central facility to have the capability of controlling the orientation of a patient inspection video, including panning up or down, right or left and actuating a zoom feature of the video lens. This feature will permit the medical practitioner remote from the emergency facility to conduct independent patient inspection and to discuss aspects of the patient's condition with the medical personnel and perhaps also with the patient during the time the local medical personnel are engaged in the conduct of independent patient care of treatment activities at the direction of the medial practitioner. It is desirable, therefore, to provide an emergency room video-conferencing system wherein a medical practitioner is enabled via a video-conferencing system to direct medical personnel at several remote locations to treat patients, particularly emergency patients, according to diagnosis and treatment controlled by the medical practitioner and further enabling the medical practitioner to inspect the condition of the patient for the purpose of diagnosis and to observe the medical treatment that is being administered by local staff personnel.

To enable a medical practitioner, especially during emergency conditions, to deliver high quality of medical care to a patient, from the standpoint of close inspection and diagnosis, and to ensure that local medical personnel, such as nursing personnel are enabled to concentrate on patient treatment, rather than expend time and effort manually positioning a video camera or a mobile emergency center cart having a video camera, it is desirable that the medical practitioner have the capability of independently causing the video camera to move as desired for efficient visual inspection of the patient, including close-up viewing of selective portions of the anatomy of the patient. It is also desirable that the medical practitioner have the capability of selectively controlling the video-conferencing camera from a remote location for video-conferencing with the nursing personnel at one or more emergency medical centers and for viewing both the patient and the nursing personnel at such one or more centers to thus ensure delivery of the highest quality medical care to the patient.

SUMMARY OF THE INVENTION

It is a principle feature of the present invention to provide a novel emergency room video-conferencing arrangement having a mobile emergency center cart that can be positioned as needed within an emergency room or other medical facility and having a video camera enabling a remotely located medical practitioner to selectively and independently control various aspects of the video camera and audio equipment to thus enable the medical practitioner to visualize and communicate with both the patient and the emergency room personnel or closely inspect the physical condition of the patient so that the medical practitioner can diagnose and control the patient's treatment and visually inspect and talk with the patient prior to and during treatment;

It is another feature of the present invention to provide a novel emergency room video-conferencing arrangement wherein the mobile emergency center cart is provided with an umbilical cord of sufficient length to enable its connection with electronic signal transmission and processing equipment connected to a wall mounted connection of a remote medical facility, thus enabling the cart to be positioned at any suitable location within an emergency room to best facilitate proper diagnosis and treatment of the patient; and Another feature of this invention to provide a novel emergency room video-conferencing arrangement wherein the emergency center cart includes positional control apparatus for the video camera thereof thus enabling the medical practitioner from a remote location to selectively position the camera or its lens equipment as needed to visualize the condition of the patient for diagnosis and to control the character of treatment that is being delivered to the patient by the medical personnel of the remote location.

It is also a feature of the present invention to provide multiple emergency centers, each having an emergency center cart with video-conferencing equipment, date transmission equipment and the like which is selectively controllable via a communications link by signals generated by a controller unit being selectively manipulated by a medical practitioner at a central office remotely located from the emergency center.

BRIEF DESCRIPTION OF THE DRAWINGS

So that the manner in which the above recited features, advantages and objects of the present invention are attained and can be understood in detail, a more particular description of the invention, briefly summarized above, may be had by reference to the preferred embodiment thereof which is illustrated in the appended drawings, which drawings are incorporated as a part hereof. It is to be noted however, that the appended drawings illustrate only a typical embodiment of this invention and are therefore not to be considered limiting of its scope, for the invention may admit to other equally effective equivalent embodiments.

In the Drawings:

FIG. 3 is a partial elevational view of the emergency center cart of FIG. 2 showing the lower and intermediate shelves thereof and further showing document illumination equipment and a document video camera for acquiring and transmitting an image of the document to the video equipment of the central office for inspection by the medical practitioner;

FIG. 4 is a pictorial illustration showing an emergency center room and showing a patient lying on a bed and being attended by a medical professional (e.g., such as nursing personnel or other non-physician medical professional) and further showing the mobile emergency center cart of the present invention being positioned for inspection of both the patient and the nursing personnel and for video-conferencing with the nursing personnel and perhaps with the patient to enable efficient and accurate diagnosis and treatment of the patient and to enable the remotely located medical practitioner (e.g., a licensed physician) to inspect and control the treatment that is being delivered to the patient by the nursing personnel;

FIG. 13 is an elevational view showing an emergency center video-conferencing cart located within an emergency center room and farther showing the overhead support and cable positioning system of FIG. 12;

FIG. 14 is a side elevational view showing a hand-held infra-red remote control unit having a funnel attachment for restricting IR radiation pattern to a narrow beam to enable selective control of the plurality of video-conferencing units of the medical control center of FIG. 5;

FIG. 15 a plan view of the hand-held infra-red remote control unit of FIG. 14; and FIG. 16 is an end view of the hand-held infra-red remote control unit of FIGS. 14 and 15.

DETAILED DESCRIPTION OF PREFERRED EMBODIMENT

Figure 1:
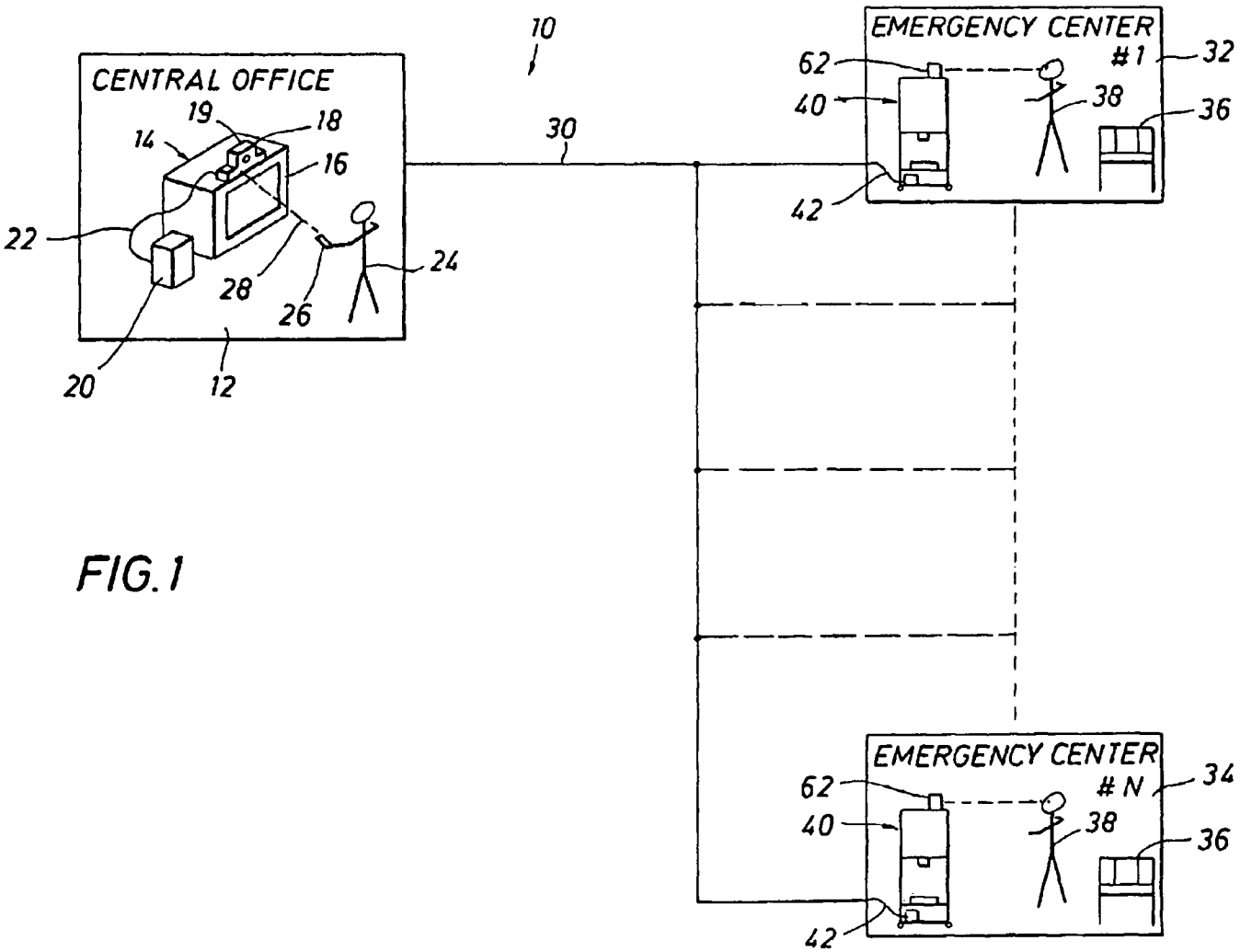
FIG. 1 is a schematic illustration showing a central office having a video-conferencing system and having a control console for actuation by or for a medical practitioner and with the video-conferencing system being connected via communications link with one or more remotely located emergency centers each having a mobile video-conferencing cart and medical personnel therein.

Referring now to the drawings and first to FIG. 1 an emergency room video-conferencing arrangement, according to the principles of the present invention, is shown generally at 10 and may conveniently take the form of a central office facility 12 within which is located a video-conferencing unit shown generally at 14 having a video monitor 16 and a video camera 18 having an electronic remotely controlled signal receiving and transmitting system 19 for video and audio communication via a communications link with a remotely located video-teleconferencing unit. A speaker 20 is shown to be connected by a speaker circuit cord 22 to the remote controlled signal receiver and transmitter or to the video monitor system, its function being to provide audio signals to and from the remote emergency room locations so that the medical practitioner 24 is enabled to audibly communicate with nursing or medical personnel at the remote location and also to communicate with the patient so that proper diagnosis of the patient's condition can be efficiently and accurately determined. The medical practitioner 24, typically a licensed medical doctor, is provided with a controller unit 26 enabling electronic control signals 28 to be transmitted to the signal receiver and transmitter portion of the video-teleconferencing control unit 18. The controller unit 26 is preferably a hand-held unit capable of transmitting signals in the form of an infra-red (IR) beam to the integrated video-teleconferencing control unit 19 for controlling one or more video-teleconferencing units of remotely located emergency room facilities or the like via one or more communications links.

The integrated video-conferencing control unit 19 is connected via appropriate electronic circuits to a communications link circuit 30 which is in selective communication with the video-teleconferencing units of a selected one of two or more remotely located emergency room facilities 32-34. The controller device 26, operated by the medical practitioner 24, is capable of being manually controlled to individually select the equipment of one or more of the emergency room facilities 32-34 as needed to diagnose and treat patients located therein. As shown at the upper right hand portion of FIG. 1, a typical emergency center room 32 is provided with a bed or gurney 36 on which is located a patient undergoing emergency treatment. Each emergency room facility will be provided with one or more medical personnel 38 (such as a nurse or other non-physician medical professional) who provide hands-on treatment of the patient under the direction of the medical practitioner 24 (such as a licensed physician), utilizing information communicated by the medical practitioner 24 via the video-conferencing system. Conversely, the medical practitioner 24 is enabled to utilize information communicated visually and audibly as well as by other communication links, such as medical data telemetry, so that proper diagnosis of the patient may be established to thereby facilitate the same medical treatment that would occur as if the medical practitioner were present in the emergency room. The medical practitioner is in video and audio communication with the nursing personnel 38 and is in video and audio communication with the patient on bed 36, if needed, and can inspect the medical treatment during its progress by independently controlling the video-conferencing equipment of the emergency center from the central office facility. To ensure that the nursing personnel can concentrate on the patient's treatment, and to also ensure that the nursing personnel 38 will not have to touch the video-conferencing equipment and can more adequately maintain the necessary sterile conditions for quality patient care, the medical practitioner 24 has the capability of independently controlling various aspects of the video-conferencing system, so that the nursing personnel 38 should have no need to touch the video-teleconferencing system after it has been properly positioned to accommodate the patient care that is being administered.

Each emergency room facility is also provided with a mobile emergency center cart, shown generally at 40, which connected to the communications link circuit 30 via an umbilical cord 42 which is typically received by an umbilical cord connection mounted to the wall structure of the emergency room facility. The emergency center cart 40 may be powered by an electrical circuit contained within the umbilical cord 42 and by connection to the electrical power circuitry of the emergency room system. Other electrical or electronic conductors of the umbilical cord 42 will provide video and audio communications links to enable the medical practitioner 24 to be in visual and audio communication with both the nursing personnel 38 and the patient and to likewise provide the nursing personnel with both video and audio communication with a medical practitioner so that diagnosis and treatment of the patient can be conducted efficiently. The umbilical cord of the emergency center cart will also have electronic conductors for telemetry of medical data representing the vital signs of the patient, thus enabling the medical practitioner to consider all relevant patient data that is desirable for patient diagnosis and treatment.

Figure 2:
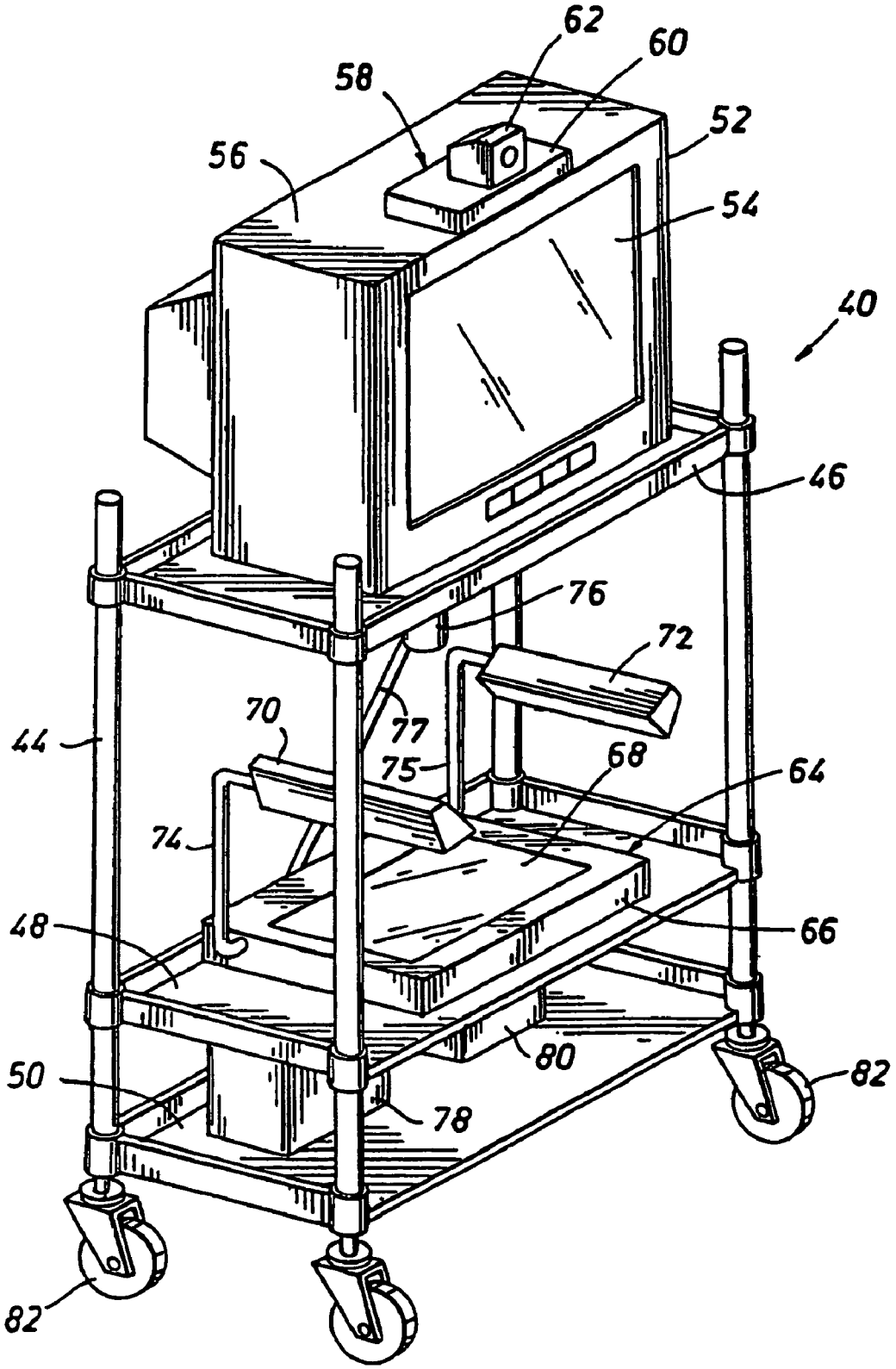
FIG. 2 is an isometric illustration of a mobile emergency center cart constructed in accordance with the principles of the present invention and having a video-conferencing arrangement including a videoconference camera and microphone, a video-conference monitor and speaker being supported by an upper shelf and having an intermediate shelf supporting a document illumination device such as for inspecting various documents such as x-ray film, EKG's, lab reports, etc., and further having a lower shelf providing space for communication and power terminal equipment.

Referring now to FIG. 2, an emergency center cart (EC cart) is shown generally at 40 and incorporates a plurality of upright structural members 44 which provide support for upper, intermediate and lower support shelves or platforms 46, 48 and 50. These support shelves may be adjustable relative to the upright structural members to properly position the video-conferencing equipment relative to the height of the nursing personnel. The upper support platform or shelf 46 provides support for a video monitor 52 and is located at an elevation so that the video screen 54 of the monitor 52 is located at an efficient viewing height, typically eye level, for nursing or medical personnel standing in the emergency room. The upper surface 56 of the video monitor 52 provides a support surface for a video-conferencing unit shown generally at 58 having an electronic signal transmitting receiving and processing unit 60 to which is controllably coupled a video camera 62. The video camera 62 may itself be movable relative to the electronic signal transmitting receiving and processing unit 60 or, in the alternative or additionally, the video camera 62 may be provided with a movable lens system enabling its field of view to be selectively positioned by electronic controlled signals generated by the controller 66 under the control of the medical practitioner 24. Additionally, the lens of the video-conferencing camera may be adjustable for panning up, down, left and right and for zooming so that the medical practitioner can efficiently inspect the patient and communicate both audibly and visually with the nursing personnel or other health care professionals of the emergency center.

The intermediate support platform or shelf 48 is provided for support of a document illumination device shown generally at 64 having a housing structure 66 within which may be located one or more illumination devices such as incandescent or fluorescent lighting elements. The housing will be provided with a light transparent or translucent screen or document support plate member 68 through which light may be transmitted for illumination of the image of an x-ray film or the like. The document support screen or plate member 68 also provides for support of other relevant medical data documents such as EKG's, lab reports, etc., that may be visibly inspected by a document camera. For lighting such other documents, a pair of lighting elements 70 and 72 are shown to be positioned by support members 74 and 75, respectively, which extend upwardly from the housing structure 66 of the document illumination device 64. A document inspection video camera 76 may be supported by the lower portion of the upper shelf or platform 46 but preferably by a boom arm 77 from housing 66 and is positioned so that its lens is directed to and focused on the screen or plate 68 of the document illumination device. Thus, whether the document is an x-ray film, an EKG, a lab report or any other type of document or whether it must be lighted or backlighted to be readable, it may be inspected by the medical practitioner at the central office location simply by appropriately manipulating the control device 66 and selecting operation of the document video camera 76 together with one or both of the internal lighting devices and external lighting devices of the document illumination device 64. The intermediate support platform may also be adjustably connected to the support structures to enable selective positioning of the document support and lighting device relative to the document video camera.

In the event the document video camera 76 should have a fixed lens, the position of the support platform or shelf 48 is adjustable relative to the upright structural members 44 so that the screen or plate 68 or any document located on the plate will be precisely in focus. If the document supported by the screen 68 should have a particular dimension so that its upper surface is out of focus with respect to the lens of the video camera 76 then the support shelf 48 will be adjusted downwardly or upwardly so as to bring the appropriate surface into focus. Obviously, for efficiency of inspection of such documents by the medical practitioner from a remote location, the lens of the video camera 76 is preferably adjustable to achieve focus from the level of the screen or plate 68 upwardly to a level several inches above the plate 68.

The lower shelf or platform 50 of the mobile emergency center cart 40 is typically fixed relative to the upright structural members 44 and provides support for various communications and power terminals 78 and 80. One or both of these communication and power terminals will be connected to umbilical cord 42. The communication and power terminals provide electrical power for operation of video and lighting equipment on the cart and also to provide for transmission of control signals from the controller unit operated by the medical practitioner through the communications link to provide for selective control of cart mounted video-conferencing apparatus.

Referring again now to FIG. 1, to illustrate the method of the invention, the medical practitioner 24 manipulates the controller device 26, which may be a handheld controller as shown or a controller console resting on a desk of the central office facility. By manipulating the controller unit the medical practitioner is enabled to select a desired communications link, via the communications link circuit 30, with a particular one of the emergency center facilities 32-34. The controller may also be selectively manipulated to establish simultaneous communications with each of the emergency room facilities if audio and video communications is needed with two or more of the emergency room facilities at any given time, as described below. Since the video-conferencing video camera 62 is positioned substantially at eye level with respect to the medical personnel 38 standing in the emergency room, the medical practitioner 24 is enabled to insure efficient interactive audio and video communication with the local medical personnel of the emergency room facility. This ensures that the information received by the medical practitioner by both video and audio is of the best possible quality. For inspection of the condition of the patient lying on the bed 36 by the medical practitioner at the central office location, the medical practitioner manipulates the electronic controller 26 to thereby adjust the position of the video camera 62 so that the patient or any selective part of the patient's anatomy can be visually inspected by the medical practitioner via the interactive communications link. The audio system of the emergency center cart 40 will also be capable of adjustment from the standpoint of volume by appropriate manipulation of the electronic controller 26 by the medical practitioner 24 so that the practitioner is enabled to communicate directly with the patient in the event the patient is capable of reporting his or her condition.

After the medical practitioner has diagnosed the patient's condition treatment of the condition can be published by the medical personnel 38 located at the emergency room facility. Since the EC cart 40 is provided with casters or other types of wheels 82 and is thus mobile, the medical personnel and the emergency room facility will be capable of moving the EC cart to a location that is desired by the medical practitioner 24 so that the best possible inspection of the patient may be accomplished. The umbilical cord 42 of the mobile EC 40 will be of sufficient length and flexibility that the EC 40 may be located virtually anywhere within the emergency room 32 . . . 34. Also, when treatment is in progress by the emergency room personnel 38, the medical practitioner 24 can inspect the treatment during its progress and thus insure that optimum professional medical treatment is being accomplished. FIG. 4 also illustrates that a nurse 38 can remotely control functions of the transmitting, receiving and processing unit 60.

Figure 5:
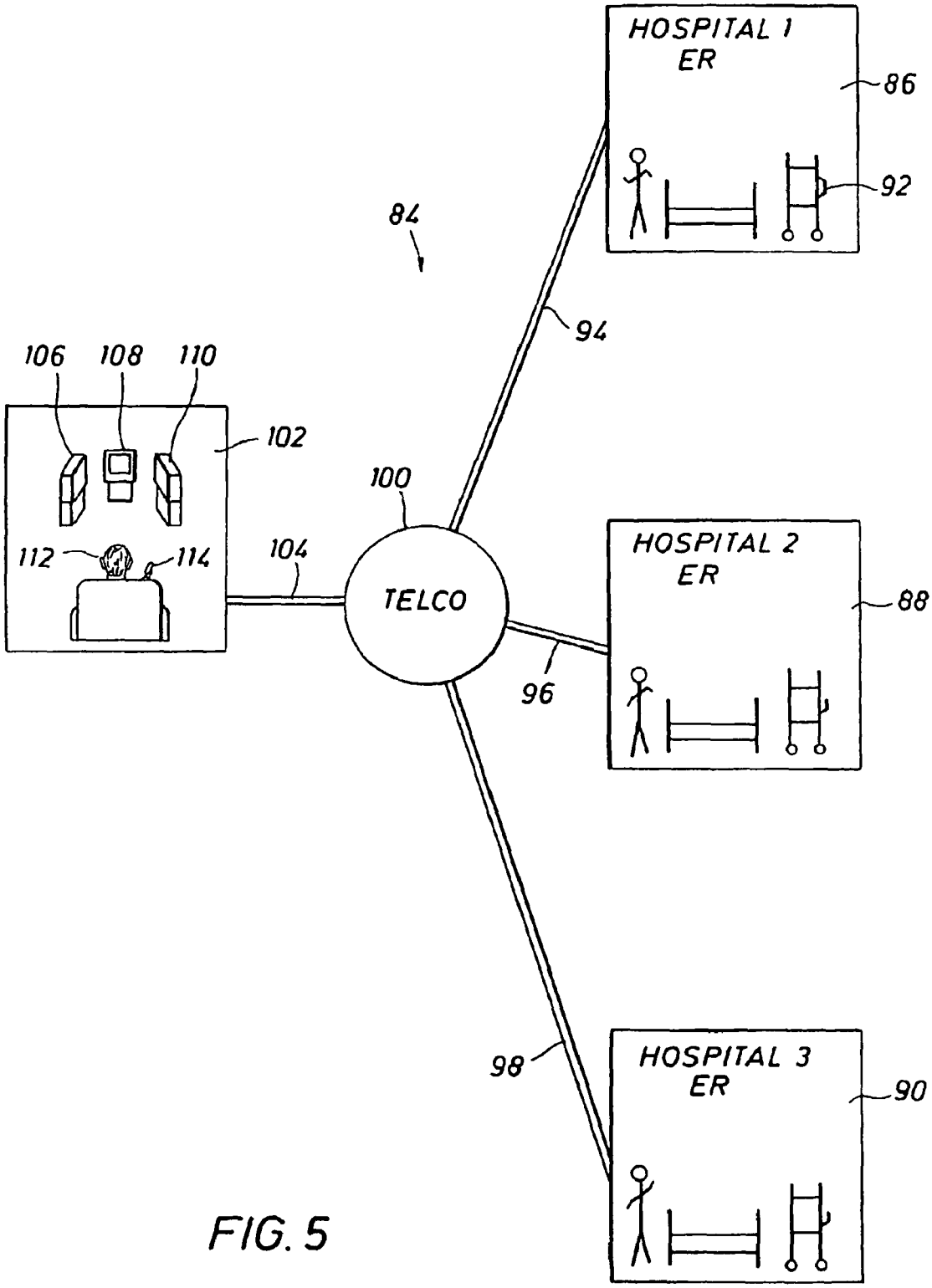
FIG. 5 is a pictorial diagrammatic illustration in plan, showing an alternative embodiment of the present invention, showing a plurality of emergency room facilities being in video-conferencing communication via a communications link with a medical control facility having a plurality of video monitors to facilitate control of emergency medical treatment of patients at a plurality of remotely located emergency room facilities by a single medical practitioner via the communications link.

Referring now to FIG. 5 a medical video-conferencing system is shown generally at 84 having a plurality of emergency center rooms 86, 88 and 90, (preferably up to five emergency center rooms) which may be remotely located from one another, such as in different parts of a city or in different locations within a geographical region. The emergency facilities are each provided with a mobile emergency video-conferencing emergency center cart (EC cart), one being shown at 92, to enable a patient to be visually and audibly evaluated and to enable nursing personnel of the emergency room to be in visual and audible communication with a medical practitioner. Each of the emergency room facilities is connected via a communications link 94, 96 and 98 to a telecommunications hub 100 and a central video-communications facility 102 which is in communication with the telecommunications hub 100 via a communications link 104. Within the central medical facility 102 is located a plurality of video monitors 106, 108 and 110 which may be simultaneously inspected by a medical practitioner 112 so that video and audio signals from the emergency center room facilities 86, 88, 90 can be simultaneously or selectively evaluated as needed. The medical practitioner is provided with a control unit 114 for controlling operations, panning and zooming of the video cameras and lenses of the mobile emergency center carts as desired for careful, direct evaluation of the patient and also of the nursing personnel and health care procedures for efficient and accurate diagnosis of the condition of the patient and inspecting treatment of the patient as instructed by the medical practitioner.

It should be understood that the communications links 94, 96, 98 and 104, shown in FIG. 5, may be hardwired electronic connections or may conveniently take any suitable form of telemetry enabling video and audio signal transmission to and from the emergency center facilities and enabling transmission of control signals to the EC carts of the individual emergency center facilities.

Figure 6:
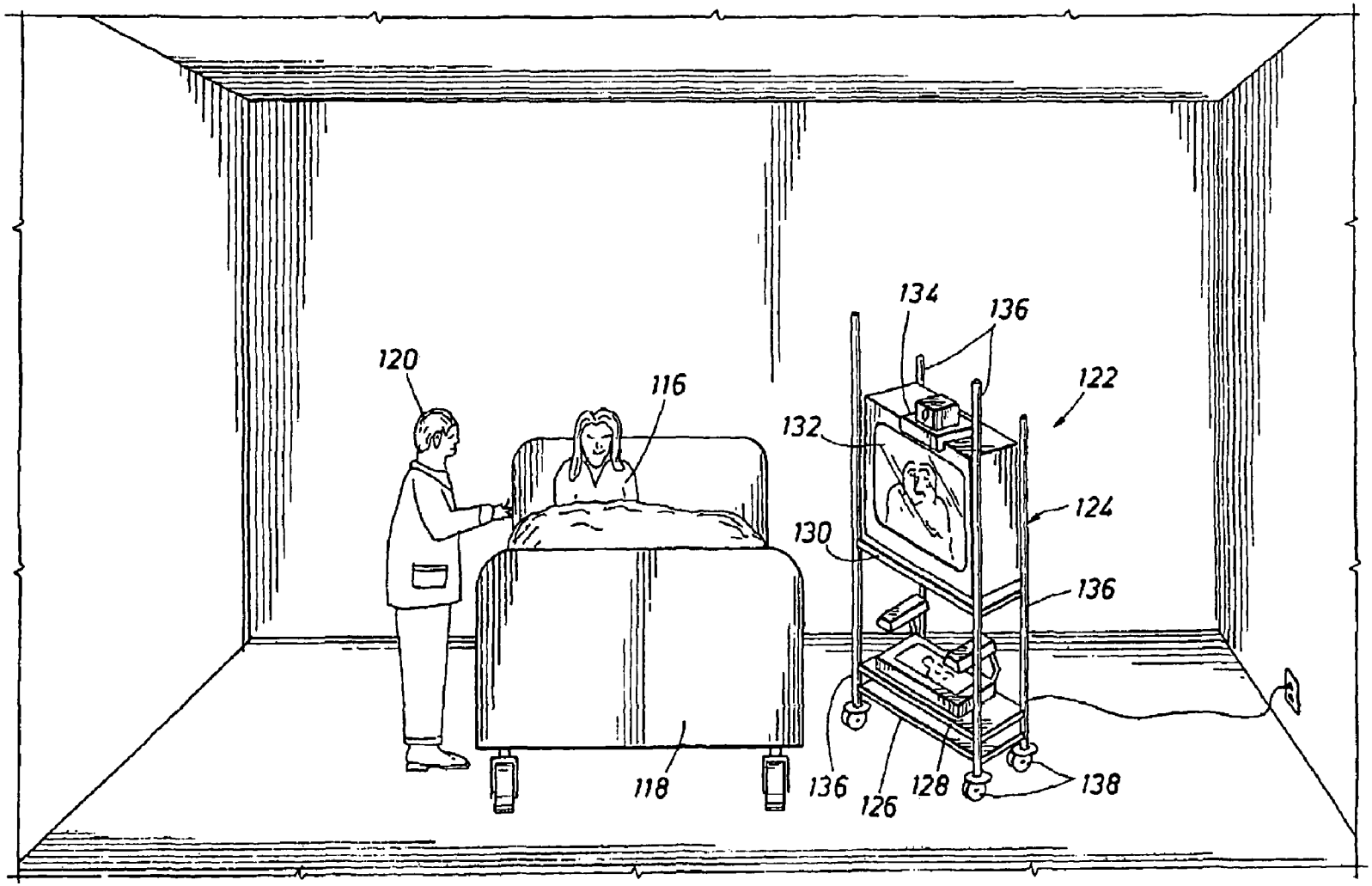
FIG. 6 is a pictorial illustration of an emergency center having a bed for a patient and having a mobile emergency center video-conferencing cart supporting video-conferencing equipment and patient data acquisition equipment and having data transmission, electrical power and video-conferencing control with a communications link via an umbilical cable.
Figure 7:
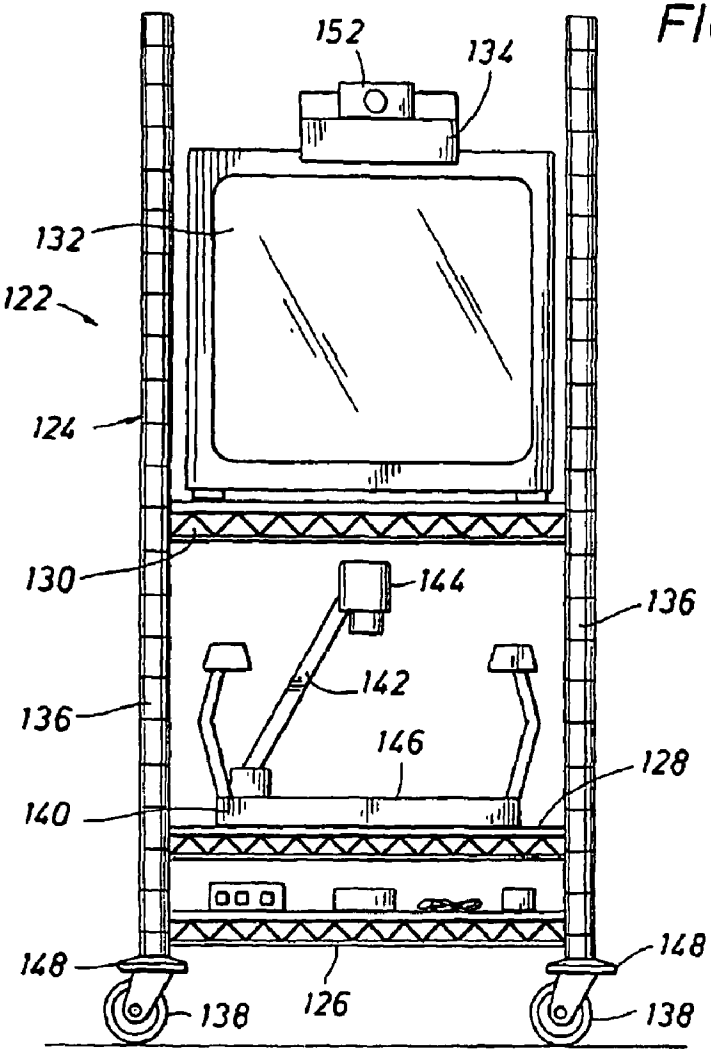
FIG. 7 is an isometric illustration showing a emergency center video-conferencing cart embodying the principles of the present invention.
Figure 10:
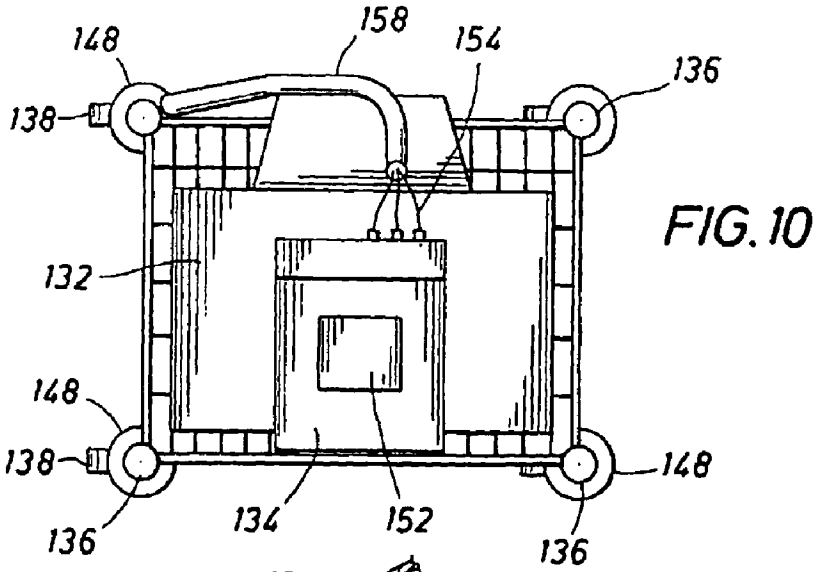
FIG. 10 is a plan view of the emergency center video-conferencing cart of FIG. 7 showing the video-conferencing unit positioned on the video monitor and showing its wiring harness.
Figure 11:
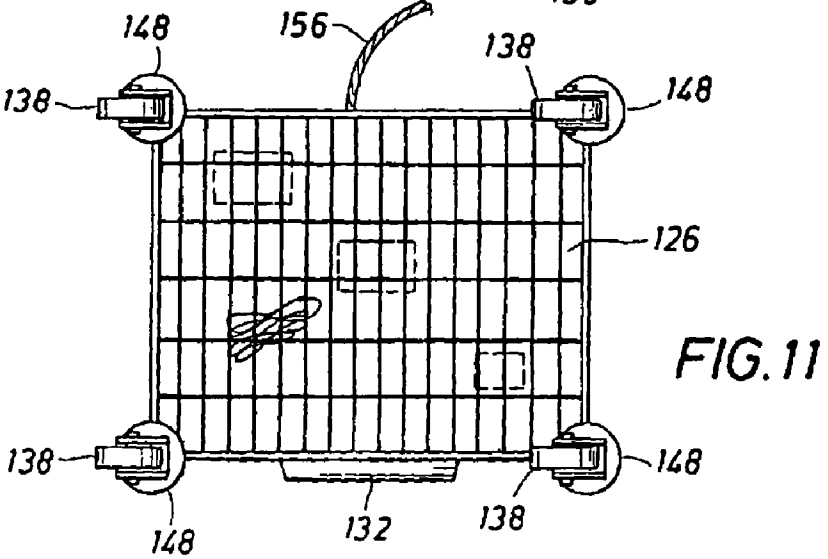
FIG. 11 is a bottom view of the emergency center video-conferencing cart of FIG. 7 showing the control electronics supported thereby and showing a portion of the umbilical cable thereof.
Figure 9:
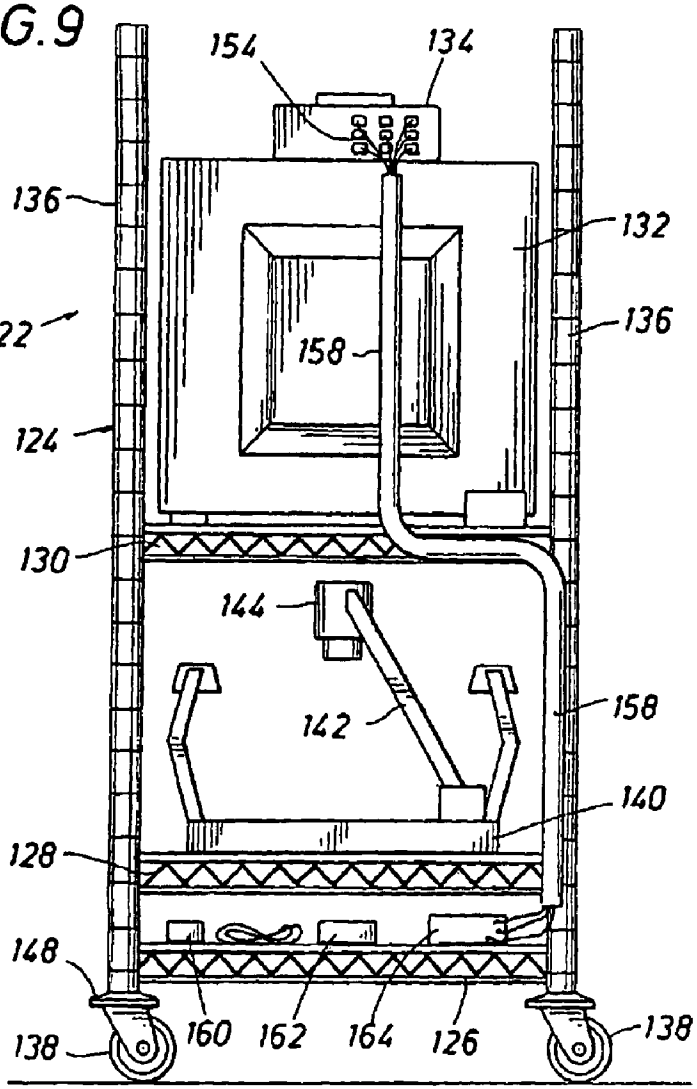
FIG. 9 is a rear elevational view of the emergency center video-conferencing cart of FIG. 7 showing further details thereof.

Referring now to FIG. 6, a perspective view is shown of one of the emergency room facilities of FIG. 5 which shows a patient 116 in a bed 118, being attended by medical personnel 120, such as a nurse practitioner, and further showing an EC cart 122 of the general character shown at 40 in FIG. 2. The EC cart 122, which is shown in greater detail in FIGS. 6-10, has a frame structure shown generally at 124 having a bottom shelf 126, an intermediate shelf 128 and an upper shelf 130. A video monitor 132 and a video-teleconferencing unit 134 are supported by the upper support shelf 130. The frame structure of the EC cart 122 is defined by four corner standards or posts 136 which provide support for the upper, intermediate and lower support shelves and also define structure to which casters or other types of wheels 138 are attached. It should be noted that the corner standards or posts 136 are of sufficient height to extend at least to or beyond the upper portion of the video monitor 132 to thus provide the monitor and the video-conferencing unit 134 with protection against being bumped by other objects within the emergency center room as the cart is moved or as other objects are moved. The corner posts also provide cart structure that can be grasped, pulled or pushed by medical personnel to change the position of the cart within the emergency center as directed by the medical practitioner. A document lighting device 140 (FIG. 7), of the character shown at 64 in FIG. 2, is supported by the intermediate support shelf 128 and may include a video camera support 142 supporting a video camera 144 in position for viewing documents positioned on the support and backlighting screen 146 of the document lighting device.

To provide the apparatus supported by the EC cart 122 with additional protection against bumping into, being bumped by or being jarred by other objects, the posts 136 of the cart are provided with resilient bumper elements 148 which may be composed of rubber or any suitable rubber-like material.

The video-teleconferencing unit 134 is provided with a video camera head 152 which is capable of being controllably tilted upwardly, downwardly and to each side for the purpose of permitting the medical practitioner to achieve video inspection of the patient and other aspects of the emergency center facility as well as having the capability of zooming the lens of the video-conferencing camera so that close inspection of any selected anatomy of the patient can be selectively viewed under the control of the medical practitioner by electronic signals transmitted from the controller unit via the communications link to one or more of the selected video-conferencing systems of the mobile EC carts.

Figure 8:
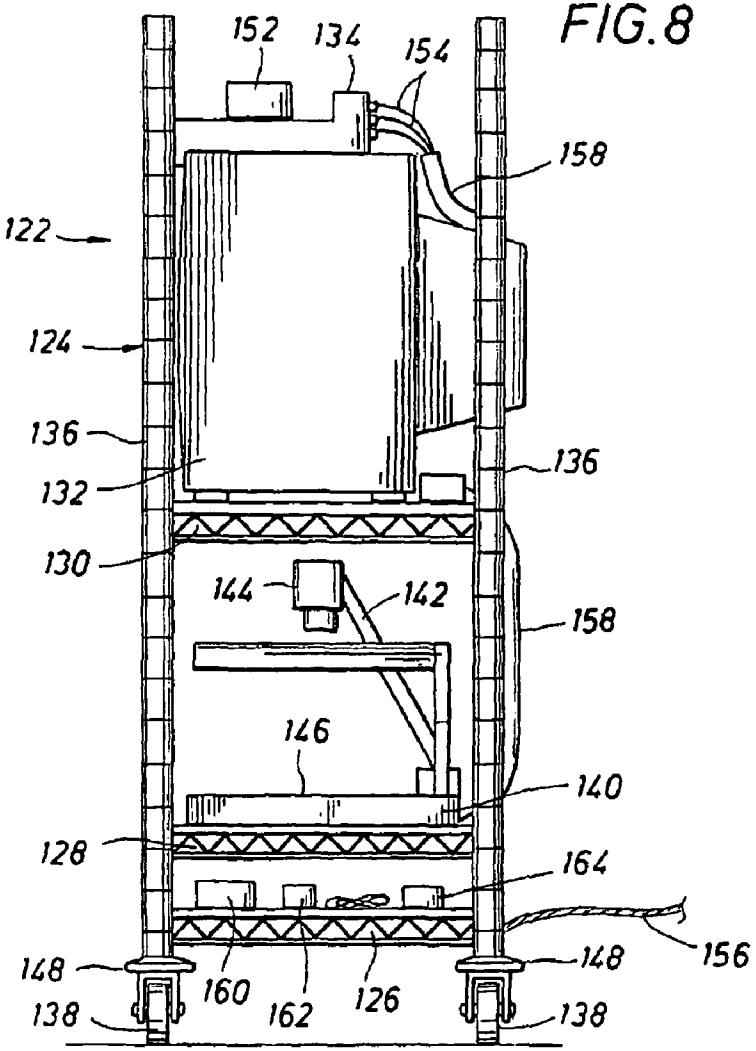
FIG. 8 is a side elevational view of the emergency center video-conferencing cart of FIG. 7 and showing additional details thereof.

The various electrical contacts or receptacles of the video-conferencing units 134 are connected by the electronic circuit wires 154 of the umbilical cable 156 as illustrated by FIG. 8. These electronic conductors are sheathed by plastic tubing 158 for protection thereof.

The lower support shelf 126 of the cart structure functions as a communications shelf for supporting various communications devices such as an IMUX inverse multiplexer 160, NT-3 power supply 162, surge protector 164, and may also support other electrical equipment such as spare electronic and video cables that may be needed.

Figure 12:
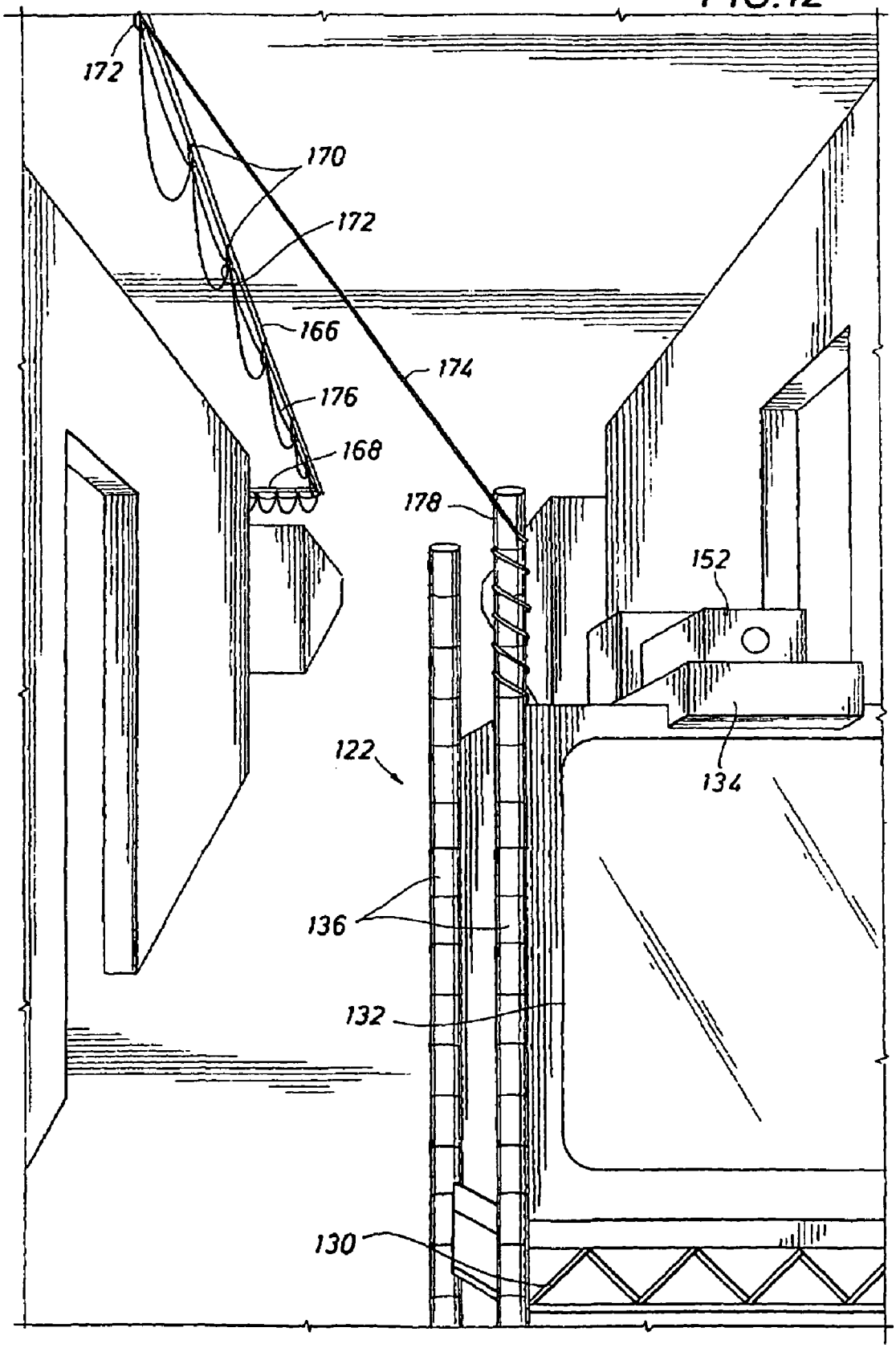
FIG. 12 is a perspective view showing the interior of an emergency room facility or the like and further showing an overhead supported umbilical cable for its power and communications.

Referring now to FIG. 12, the perspective view shows the mobile EC cart 122 being located within an emergency center facility. Since an umbilical cable of the mobile EC cart may extend across a floor and represent a hazard to persons walking in the immediate area, it is desirable to provide the emergency center facility with means for supporting the umbilical cable without diminishing the mobility of the cart. An overhead track 166 is secured to the ceiling of the room and may extend around corners as shown at 168. A plurality of plastic, preferably Nylon rollers 170 are movably received by the overhead track and are each provided with a hook element 172 for support of a guided cable 174 representing the umbilical cable of the cart 122. The guided cable 174 may additionally be supported by an elastic bungie cord 176 which assists in permitting extension and controls contraction of the umbilical cable as need for selective positioning of the cart within the emergency center. Additionally, one of the support posts of the EC cart may save as a guide post 178 which receives the power and video-conferencing control cable 174 to ensure efficient positioning thereof so that it does not interfere with personnel movement about the mobile EC cart 122.

As mentioned above, in the central medical facility 102 the medical practitioner 112 is provided with a plurality of video monitors, typically one for each of the remote emergency center facilities 86, 88, 90, etc. The control unit 114 utilized by the medical practitioner typically operates by infra-red (IR) beam transmission for sending control signals to the video camera and remote control signal receiver/transmitter 18 shown in FIG. 1. To insure that the IR signal beam is received by the video camera and remote control signal receiver/transmitter of a selected one of the plurality of video-conferencing systems 106, 108, 110, etc. monitored by the medical practitioner 112 as shown in FIG. 5, it is desirable to provide the video-conferencing remote control unit 114 with means for ensuring that the IR signal beam is sufficiently concentrated to actuate only the remote control signal receiver/transmitter that is individually selected by the medical practitioner. To ensure that the IR beam emitted from the video-conferencing remote control unit 114, an adapter funnel 180 is secured to the remote control unit in any suitable fashion, such as by means of small screws, by a suitable bonding agent, etc. The adapter funnel is of tubular form and defines a small end 182 that is fixed to the remote control unit 114 and tapers gradually to a larger end 184. The small end 182 may have a dimension of about 3 mm for intimate engagement with the transmitting end of the remote control unit. In contrast, the larger end 184 may have a dimension of about 3½ mm. The adapter funnel structure may be defined by a plurality of substantially flat panels, including upper and lower panels 186 and 188 and side panels 190 and 192. The adapter funnel may be in the order of 10 inches in length or of any other suitable length that is sufficient for suitably controlling the dimension of the emitted IR signal beam in relation to the distance from and location of the plurality of video-conferencing systems being controlled by the medical practitioner.

In view of the foregoing it is evident that the present invention is one well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, of the scope of the invention.

I claim:

1. A business method for delivery of medical services utilizing a system including a plurality of satellite medical care facilities, at least one physician disposed at a central medical video-conferencing station, and a first patient and a first medical care giver disposed in a first of said plurality of satellite medical care facilities, the method comprising the steps of:

(a) establishing a video-conferencing communications system among said *central* medical video-conferencing station and said plurality of satellite medical care facilities;

(b) selecting said first of said plurality of satellite medical care facilities to actively receive video and audio communication from said physician;

(c) controlling a video-conferencing system of said first of said plurality of satellite medical care facilities to control a video image received at said central medical video-conferencing station from said first of said plurality of satellite medical care facilities;

(d) diagnosing a medical condition of said first patient at said first of said plurality of satellite medical care facilities by said physician from said central medical video-conferencing station;

(e) providing instructions via said video-conferencing system to said first medical caregiver by said physician to treat said first patient at said first of said plurality of satellite medical *care* facilities;

(f) selecting a second of said plurality of satellite medical care facilities to actively receive video and audio communication from said physician;

(g) displaying an image of a second patient disposed at said second of said plurality of satellite [emergency] *medical* care facilities at said central medical video-conferencing station;

(h) controlling a video-conferencing system of said second of said plurality of satellite medical care facilities to control said image received at said central medical video-conferencing station from said second of said plurality of satellite medical care facilities;

(i) diagnosing a medical condition of said second patient by said physician from said central medical [videoconferencing] *video-conferencing* station; and (j) providing instructions via said video-conferencing system to a second medical caregiver disposed at said second of said plurality of satellite medical care facilities by said physician to treat said second patient generally contemporaneously with said steps of diagnosing said medical condition of said first patient and providing instructions to said first medical caregiver.

2. The method of claim 1 further comprising the steps of:

controlling said video-conferencing system of said first of said plurality of satellite medical care facilities; then controlling said video-conferencing system of said second of said plurality of satellite medical care facilities.

3. The method of claim 1 further comprising the steps of:

controlling said video-conferencing system of said first of said plurality of satellite medical care facilities, and simultaneously controlling said video-conferencing system of said second of said plurality of satellite medical care facilities.

4. A business method for delivery of emergency medical services utilizing a system including first and second emergency care facilities, an emergency room physician disposed at an emergency medical video-conferencing station, a first patient and a first skilled medical caregiver disposed at said first emergency care facility, and a second patient and a second skilled medical caregiver disposed at said second emergency care facility, the method comprising the steps of:

(a) establishing a first video-conferencing communication link between said emergency medical video-conferencing station and said first emergency care facility;

(b) establishing a second video-conferencing communication link between said emergency medical video-conferencing station and said second emergency care facility;

(c) displaying an image of said first patient on a first monitor disposed in said emergency medical video-conferencing station via said first video-conferencing communication link;

(d) viewing said image of said first patient by said emergency room physician;

(e) controlling a video-camera disposed in said first emergency care facility from said emergency medical video-conferencing station to control said image of said first patient;

(f) aiding a treatment of a medical condition of said first patient at said first emergency care facility by said emergency room physician from said emergency medical video-conferencing station;

(g) displaying an image of said second patient at said emergency video-conferencing station via said second video-conferencing communication link;

(h) controlling a video-camera disposed in said second emergency care facility from said emergency medical videoconferencing station to control said image of said second patient; and (i) aiding a treatment of a medical condition of said second patient at said second emergency care facility from said emergency medical video-conferencing station contemporaneously with said step of aiding the treatment of said first patient.

5. The method of claim 4 further comprising the steps of:

selectively displaying said image of said first patient on said first monitor; and selectively displaying said image of said second patient on said first monitor.

6. The method of claim 5 further comprising the steps of:

selectively viewing said image of said first patient by said emergency room physician on said first monitor;

selectively viewing said image of said second patient by said emergency room physician on said first monitor; and aiding the treatment of said medical condition of said second patient at said second emergency care facility by said emergency room physician from said emergency medical video-conferencing station contemporaneously with said step of aiding the treatment of said first patient.

7. The method of claim 4 further comprising the step of:

displaying said image of said second patient on a second monitor disposed in said emergency medical video-conferencing station while simultaneously displaying said image of said first patient on said first monitor.

8. The method of claim 7 further comprising the steps of:

selectively viewing said image of said first patient by said emergency room physician on said first monitor;

selectively viewing said image of said second patient by said emergency room physician on said second monitor; and aiding the treatment of said medical condition of said second patient at said second emergency care facility by said emergency room physician from said emergency medical video-conferencing station contemporaneously with said step of aiding the treatment of said first patient.

*9. A system for delivering medical evaluation services comprising:*

*a video conferencing arrangement including a camera, monitor and controller located at a central medical video conferencing station;*

*a first remotely controllable video camera located at a first satellite medical care facility, which is one of a plurality of satellite medical care facilities which are geographically remotely located from each other and from said central medical video conferencing station;*

*a second remotely controllable video camera located at a second of said plurality of satellite medical care facilities;*

*a first audio-video conferencing communication link established between said central medical video conferencing station and said first satellite medical care facility, said first audio-video communication link enabling a medical practitioner to confer audibly with a first patient or a first care giver at said first satellite medical care facility;*

*a second audio-video conferencing communication link established between said central medical video conferencing station and said second satellite medical care facility, said second audio-video communication link enabling said medical practitioner to confer audibly with a second patient or a second care giver at said second satellite medical care facility;*

*said controller enabling said medical practitioner at said central medical video conferencing station to control a first video image of said first patient from said first camera at said first satellite medical care facility and view said first video image of said first patient at said central medical video conferencing station; and*

*said controller enabling said medical practitioner at said central medical video conferencing station to control a second video image of said second patient from said second camera at said second satellite medical care facility and view said second video image of said second patient at said central medical video conferencing station;*

*whereby said first image of said first patient and said second image of said second patient can be viewed simultaneously by said medical practitioner at said central medical video conferencing station thereby enabling said medical practitioner to professionally evaluate conditions of said first and second patients generally contemporaneously and to confer regarding evaluations with said first and second patients or said first and second care givers at said satellite medical care facilities.*

*10. The system of claim 9 in which:*

*said central medical video conferencing station includes first and second video monitors; whereby*

*said first video image can be displayed on said first video monitor simultaneously when said second video image is displayed on said second video monitor.*

*11. The system of claim 9 in which:*

*said first satellite medical care facility is a first emergency care facility; and*

*said second satellite medical care facility is a second emergency care facility.*

*12. An arrangement for diagnosing emergency medical conditions of patients comprising:*

*a central medical video conferencing station;*

*first and second satellite emergency medical care facilities which are geographically remotely located from each other and from said central medical video conferencing station;*

*a first video camera located at said first satellite emergency medical care facility;*

*a second video camera located at said second satellite emergency medical care facility;*

*a first video conferencing communication link established between said central medical video conferencing station and said first satellite emergency medical care facility which enables a first video image from said first video camera of a first patient at said first satellite emergency medical care facility to be displayed at said central medical video conferencing station; and*

*a second video conferencing communication link established between said central medical video conferencing station and said second satellite emergency medical care facility which enables a second video image from said second video camera of a second patient at said second satellite emergency medical care facility to be displayed at said central medical video conferencing station simultaneously with display of said first video image at said central medical video conferencing station;*

*whereby medical conditions of said first and second patients can be evaluated substantially simultaneously by an emergency room physician at said central medical video conferencing station.*

*13. The arrangement of claim 12 further comprising:*

*a control arrangement by which said first video camera at said first satellite emergency medical care facility and said second video camera at said second satellite emergency medical care facility can be controlled by said emergency room physician at said central medical video conferencing station, so as to produce different first and second video images of said first and second patients for evaluation of medical conditions.*

*14. The arrangement of claim 12 wherein:*

*said first patient is attended to by a first care giver; and*

*said second patient is attended to by a second care giver.*

*15. A method for delivering medical evaluation services by a medical practitioner using a system which includes a central medical video conferencing station, a plurality of satellite medical care facilities which are geographically remotely located from each other and from said central medical video conferencing station, a first remotely controllable video camera located at a first of said satellite medical facilities, and a second remotely controllable video camera located at a second of said satellite medical care facilities, the method comprising the steps performed by or on behalf of a licensed medical practitioner of:*

*using a first audio-video conferencing communication link between said central medical video conferencing station and said first satellite medical care facility to confer visually and audibly with a first patient or a first care giver at said first satellite medical care facility;*

*using a second audio-video conferencing communication link between said central medical video conferencing station and said second satellite medical care facility to confer visually and audibly with a second patient or a second care giver at said second satellite medical care facility;*

*controlling said first video camera from said central medical video conferencing station to produce a first video image at said central medical video conferencing station of said first patient at said first satellite medical care facility;*

*controlling said second video camera from said central medical video conferencing station to produce a second video image at said central medical video conferencing station of said second patient at said second satellite medical care facility; and*

*viewing said first image of said first patient and said second image of said second patient simultaneously at said central medical video conferencing station thereby enabling the medical practitioner to professionally evaluate conditions of said first and second patients generally contemporaneously and to confer regarding evaluations with at least one of the group consisting of said first patient, said second patient, said first care giver, and said second care giver.*

*16. The system of claim 15 in which said central medical video conferencing station includes first and second video monitors, the method further comprising the step of:*

*displaying said first video image on said first video monitor and simultaneously displaying said second video image on said second video monitor.*

*17. The system of claim 15 in which:*

*said first satellite medical care facility is a first emergency care facility; and*

*said second satellite medical care facility is a second emergency care facility.*

*18. A method for providing professional medical evaluation services comprising the steps of:*

*establishing a central video-conferencing communications station;*

*enabling simultaneous video-conferencing connections between said central video-conferencing station and a geographically remote first medical care facility via a first video-conferencing link and between said central video-conferencing station and a geographically remote second medical care facility via a second video-conferencing link, said first medical care facility being geographically remote from said second medical care facility;*

*enabling simultaneous display at said central video-conferencing station of a first image of a first patient located at said first medical care facility with a first care giver and a second image of a second patient located at said second medical care facility with a second care giver;*

*enabling contemporaneous professional medical evaluation of said first and second patients from said central video-conferencing station via said first and second video-conferencing links;*

*enabling audio and video communication of professional medical evaluation from said central video-conferencing station to said first patient or said first medical care giver via said first video-conferencing link; and*

*enabling audio and video communication of professional medical evaluation from said central video-conferencing station to said second patient or said second medical care giver via said second video-conferencing link.*

*19. The method of claim 18 further comprising the steps of:*

*enabling control from said central video-conferencing station of a first camera located in said first medical care facility via said first video-conferencing link; and*

*enabling control from said central video-conferencing station of a second camera located in said second medical care facility via said second video-conferencing link.*

*20. The method of claim 18 further comprising the step of:*

*enabling contemporaneous professional medical diagnosis of said first and second patients from said central video-conferencing station via said first and second video-conferencing links by an emergency room physician.*

* * * * *

US00RE42288C1

(12) EX PARTE REEXAMINATION CERTIFICATE (10035th)

United States Patent

Degioanni

(10) Number: US RE42,288 C1

(45) Certificate Issued: Feb. 12, 2014

(54) EMERGENCY FACILITY VIDEO-CONFERENCING SYSTEM

(75) Inventor: Joseph J. Degioanni, Houston, TX (US)

(73) Assignee: Emtel, Inc., Houston, TX (US)

Reexamination Request:
No. 90/012,415, Sep. 7, 2012

Reexamination Certificate for:

| | |
|---|---|
| Patent No.: | **Re. 42,288** |
| Issued: | **Apr. 12, 2011** |
| Appl. No.: | **12/290,124** |
| Filed: | **Oct. 24, 2008** |

Related U.S. Patent Documents

Reissue of:

| | |
|---|---|
| (64) Patent No.: | **7,129,970** |
| Issued: | **Oct. 31, 2006** |
| Appl. No.: | **10/396,635** |
| Filed: | **Mar. 25, 2003** |

Related U.S. Application Data

(63) Continuation of application No. 10/118,445, filed on Apr. 8, 2002, now abandoned, which is a continuation of application No. 09/527,774, filed on Mar. 17, 2000, now Pat. No. 6,369,847.

(51) Int. Cl.
*H04N 7/14* (2006.01)

(52) U.S. Cl.
USPC ..... 348/14.01; 348/14.05; 348/14.08; 348/14.09; 379/106.02; 600/300

(58) Field of Classification Search
None
See application file for complete search history.

(56) References Cited

To view the complete listing of prior art documents cited during the proceeding for Reexamination Control Number 90/012,415, please refer to the USPTO's public Patent Application Information Retrieval (PAIR) system under the Display References tab.

*Primary Examiner* — Eron J Sorrell

(57) ABSTRACT

A medical video-teleconferencing and treatment system, having a central video-conferencing station and one or more remote video-conferencing stations and a communications link establishing video-conferencing communication therebetween, A central video monitor and audio system is located at the central video-conferencing station, and a controller unit is coupled with the communications link. The remote video-conferencing stations each have a mobile emergency center cart including a remote video monitor and audio system and a video-conferencing camera controlled by the controller unit via the communications link and capable of responding to control signals of the controller unit for panning and zoom movement of said video-conferencing camera by a medical practitioner located at the central video-conferencing station. The arrangement enables the medical practitioner to observe and to diagnose the condition of the patient and direct the medical personnel of the selected video-conferencing station to provide treatment of the patient.

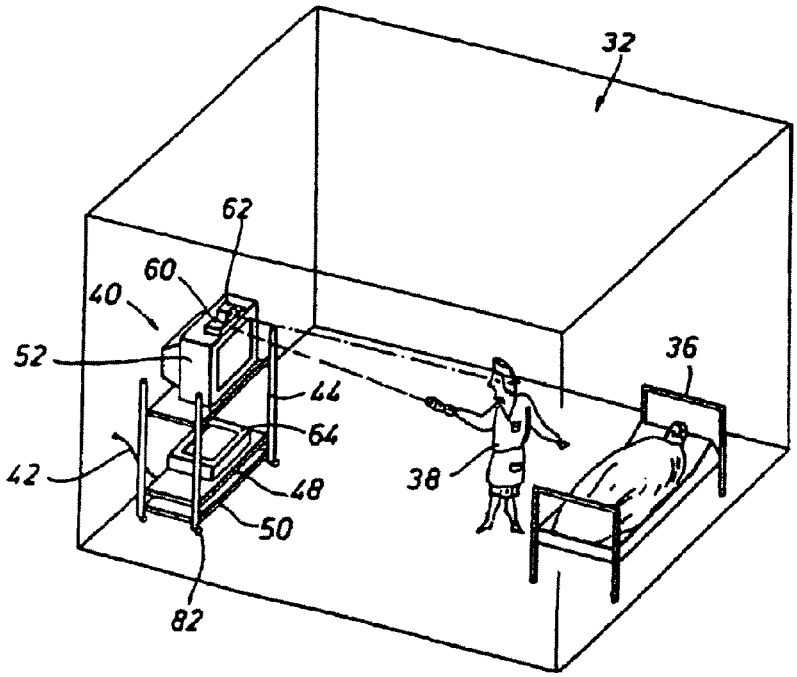

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-20 is confirmed.

* * * * *